Feb. 27, 1973 B. L. COBIA Plant Pat. 3,310

MILKWEED PLANT

Filed May 18, 1971

INVENTOR
BARNELL L. COBIA
BY Roger L. Martin
ATTORNEY

United States Patent Office

Plant Pat. 3,310
Patented Feb. 27, 1973

3,310

MILKWEED PLANT

Barnell L. Cobia, 135 Temple Grove Drive,
Winter Garden, Fla. 32787

Filed May 18, 1971, Ser. No. 144,693
Int. Cl. A01h 5/00
U.S. Cl. Plt.—88 1 Claim

ABSTRACT OF THE DISCLOSURE

A new and distinct plant variety of the milkweed family is structurally closely similar in appearance to plant specimens of the *Hoya carnosa compacta* variety but is distinguished from the latter variety by characteristic leaf blade border variegations.

The invention relates to a new and distinct plant variety of the milkweed (Asclepiadaceae) family and which has been named the *Hoya carnosa compacta* (cv) Marginalis by the inventor.

Certain plants of the milkweed family are well known in the foliage plant market and among these are those of the *Hoya carnosa compacta* variety. A lesser known related variety found in the marketplace but which is rapidly gaining popularity is the *Hoya carnosa compacta* (cv) Mauna Loa variety and which forms the subject matter of the inventor's co-pending application, Ser. No. 808,025, filed Mar. 13, 1969.

Plants of the *Hoya carnosa compacta* variety have a compact growth habit with leaf blades which generally fold along the midrib of the blade and which have a solid green field which encompasses the entire upper epidermal area of the blade. Plants of the *Hoya carnosa compacta* (cv) Mauna Lao variety are structurally closely similar in appearance to plant specimens of the *Hoya carnosa compacta* variety but are readily distinguishable from the latter variety by characteristics which, among others, provide variegated leaf blades that have an albino center field which is surrounded by a green border area.

A substantial segment of the purchasing public has a preference for plants which exhibit variegated leaf blade characteristics and a general object of the invention has been to develop a plant variety which is related to both the *Hoya carnosa compacta* variety and the *Hoya carnosa compacta* (cv) Mauna Loa variety but which is readily distinguished by the purchasing public from such varieties by variegated leaf blade characteristics. The object of the invention has been fully realized as will be evident from the following detailed disclosure.

Plants of the new variety generally resemble plants of the *Hoya carnosa compacta* variety in structural appearance but are distinguished from this variety by variegated leaf blades which have albino border areas in the upper and lower epidermal areas of the leaf blades and which generally surround solid green center fields. The new variety is distinguishable from specimens of the *Hoya carnosa compacta* (cv) Mauna Loa variety for reasons which are apparent from the following disclosure and from the plant description set forth in the aforementioned application. The new variety, as such, is mainly distinguished from its antecedents and related varieties known to the inventor by a growth habit providing specimens with structural characteristics that are normally identified with plant specimens of the *Hoya carnosa compacta* variety and with variegated leaf blades characterized by albino border areas that surround generally solid green center fields in the upper and lower epidermal blade parts, as will be more apparent from the disclosure which follows.

The new variety appeared as a sport on a plant specimen of the *Hoya carnosa compacta* variety which was under cultivation in a nursery at Winter Garden, Fla., and since the initial discovery of the new variety, has been asexually reproduced by the inventor at the Winter Garden nursery by the propagation of stem cuttings taken from the original plant specimen. Through successive propagations it has been ascertained that plants of the new variety closely resemble plant specimens of the *Hoya carnosa compacta* variety in structural appearance but are distinguishable from this plant variety and from other related varieties known to the inventor by a growth habit which provides such structural similarity normally identifiable with plant specimens of the *Hoya carnosa compacta* variety and variegated leaf blades that are characterized by an albino border areas which surround generally solid green center areas in the upper and lower epidermal areas of the blade.

The accompanying drawings serve, by color photographic means, to illustrate the new variety and wherein.

Figure 1:
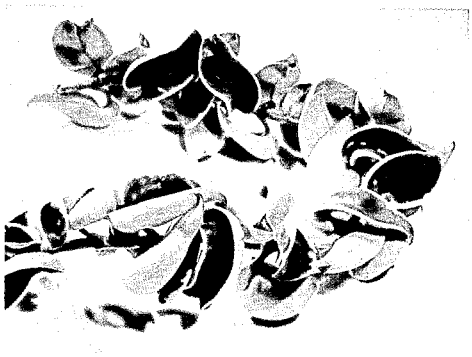
FIG. 1 is a color photograph of a vine cut from a plant specimen of the new variety.
Figure 2:
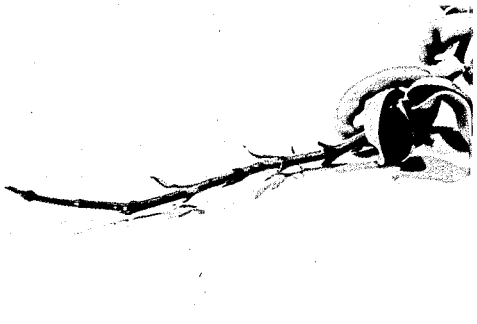
FIG. 2 is a color photograph of a plant specimen of the new variety showing immature growth at the tip of the vine of the specimen.
Figure 3:
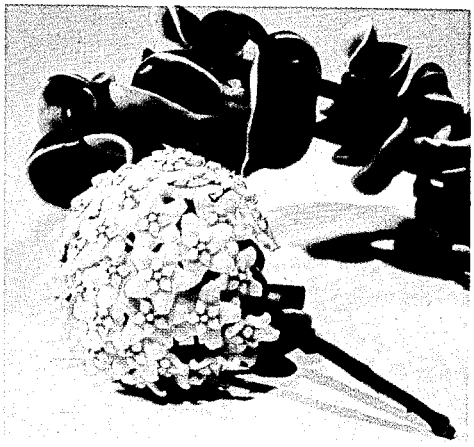
FIG. 3 is a color photograph showing inflorescences on a vine of the new variety with one inflorescence having flowers which have opened whereas the other inflorescence shows the flowers prior to opening.
Figure 4:
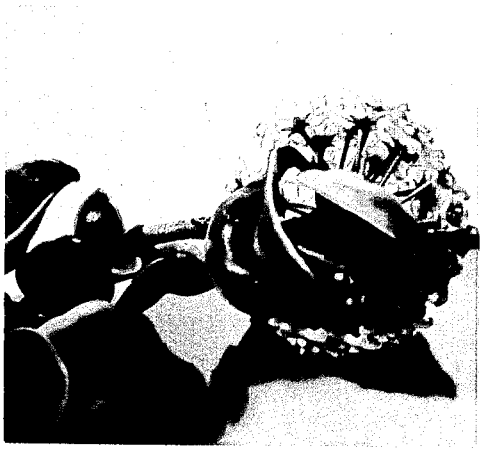
FIG. 4 is another color photograph of one of the inflorescences seen in FIG. 3.

The following is a detailed description of the new plant variety with colors and hues, unless otherwise clearly indicated by the text, being named in accord with the ISCC–NBS method of designating colors (U.S. Department of Commerce, National Bureau of Standards, Circular 553, issued Nov. 1, 1955), the named colors being interpreted from color notations derived by comparison with color specimens in the current "Neighboring Hues Edition" of the Munsell Book of Color, published by the Munsell Color Company, Inc., of Baltimore, Md.

*Plant description*

Name: *Hoya carnosa compacta* (cv) Marginalis.

Origin: A sport on a plant specimen of the *Hoya carnosa compacta* variety.

Classification:

(*A*) *Botanic.*—(Ascleipiadecease) milkweed family.

(*B*) *Commercial.*—Foliage plant.

Form: Semisucculent, tropical, twining vine type perennial evergreen with some branching.

Stems:

(*A*) *General.*—Caulescent, fleshy, herbaceous with structural characteristics normally identifiable with the *Hoya carnosa compacta* variety.

(*B*) *Texture.*—Moderately pubescent during immaturity and with age becoming glaucous and ultimately covered with thick waxy scale.

(*C*) *Size.*—(1) Diameter: usually between 2 and 6 mm. for mature stems during the first year of vine growth from break. (2) Internode: usually between 8 and 30 mm. for mature stems during the first year of vine growth from break.

(*D*) *Color.*—Commonly dark grayish reddish brown (2.5 YR 2/2) (10 R 2/2), grayish reddish brown (2.5 YR 3/2), dark grayish brown (5 YR 2/1), grayish brown (5 YR 3/2), dark grayish yellowish brown (10 YR 3/2), brownish gray (10 YR 3/1), moderate olive brown (2.5 Y 4/2) (2.5 Y 3/2), olive gray (5 Y 3/1), moderate olive (7.5 Y 4/4), grayish olive (5 Y 3/2) and/or light olive (10 Y 5/4) (10 Y 5/6) prior to becoming glaucous.

Leaves:

(*A*) *General.*—Simple exstipulate with structural characteristics normally identifiable wtih the *Hoya carnosa compacta* variety.

(*B*) *Arrangement.*—Opposite.

(*C*) *Margins.*—Entire.

(*D*) *Venation.*—Pinnate.

(*E*) *Shape.*—(1) General: predominately ovate and elliptic with occasional variations. (2) Leaf apices: usually acute with some acuminate occurrences. (3) Leaf bases: usually from obtuse to cordate with some acute occurrences.

(*F*) *Petioles.*—(1) General: fleshy. (2) Texture: slightly pubescent and with age becoming glaucous and ultimately covered with thick waxy scale. (3) Size: (a) Diameter—usually between 1 and 4 mm. for mature petioles during first year of growth. (b) Length—usually between 4 and 12 mm. for mature petioles during first year of growth. (4) Color: commonly grayish purplish red (7.5 RP 4/6), dark purplish red (10 RP 3/6) 7.5 RP 3/6), moderate purplish red (7.5 RP 4/8) (10 RP 4/8), grayish red (2.5 R 5/4) (2.5 R 4/6) 2.5 R 4/4) (2.5 R 5/6) (7.5 R 5/4), dark red (5 R 3/4) (2.5 R 3/6) (2.5 R 2/4) (5 R 3/6), grayish reddish brown (7.5 R 3/2) and/or moderate reddish brown (7.5 R 3/4) (10 R 3/4) at exposed side of petiole upon reaching maturity and commonly grayish yellowish brown (10 YR 4/2) (near 10 YR 4/4), moderate olive brown (2.5 Y 4/4) (2.5 Y 4/2), moderate olive (5 Y 4/4), light olive (5 Y 4/4) (7.5 Y 5/4) (10 Y 5/4) (10 Y 6/4), dark greenish yellow (10 Y 6/6), and/or moderate yellow green (2.5 GY 7/6) (2.5 GY 5/4) (2.5 GY 7/4) (5 GY 6/4) at stem side of petiole and in older growth (more than 6 months) before becoming glaucous.

(*G*) *Leaf blades.*—(1) General: semisucculent and characteristic tendency identifiable with *Hoya carnosa compacta* variety to fold along midrib in manner bringing upper epidermal blade parts into general facial confrontation with variant curling of folded parts, and distinctively characterized by variegated leaf blade patterns providing in the upper epidermal blade part a green center field area which is surrounded by an albino border area and in the lower epidermal blade part an albino border area which surrounds a green center field area. (2) Texture: (a) Upper epidermis—slightly pubescent during immaturity and with smooth waxy appearing surface during maturity. (b) Lower epidermis—moderately pubescent and heavily glaucous at maturity. (3) Size: (a) Length—usually between 30 and 70 mm. during first year of maturity. (b) Maximum width—usually between 20 and 45 mm. during first year of maturity. (4) Color: (a) Upper epidermal part—(1) Green center field area: commonly moderate olive green (2.5 GY 4/4) (5 GY 4/4) (7.5 GY 4/6) (7.5 GY 3/6) (7.5 GY 4/4) and/or moderate yellow green (2.5 GY 5/6) (5 GY 5/6) (5 GY 7/4) (7.5 GY 5/6 at maturity. (2) Albino border area: commonly strong pink (2.5 R 7/8), light pink (near 5 R 8/4) (near 2.5 R 8/4), moderate pink (near 2.5 R 8/4) (2.5 R 7/6) (5 R 7/4) (5 R 8/4), dark pink (5 R 6/6), strong yellowish pink (near 10 R 7/8), moderate yellowish pink (near 2.5 YR 7/6) (2.5 YR 8/4) (7.5 R 7/4) (near 10 R 8/4), pale yellowish pink (near 10 R 9/2), light yellowish pink (near 2.5 YR 8/4) (near 5 YR 8/4) (near 10 R 8/4), moderate orange (5 YR 7/6) (near 2.5 YR 7/6) and/or pale orange yellow (10 YR 8/4) in young mature leaves (less than 6 months old) and commonly light yellow (near 2.5 Y 8/6) (5 Y 9/6), moderate yellow (near 2.5 Y 8/6), pale yellow (5 Y 9/4) (near 2.5 Y 9/4) (near 7.5 Y 9/2), yellowish white (near 7.5 Y 9/2) (near 5 Y 9/2), pale greenish yellow (7.5 Y 9/4) (10 Y 9/4), light greenish yellow (7.5 Y 9/6) (7.5 Y 9/7), and/or pale yellow green (10 Y 9/2) in older growth after fading. (b) Lower epidermal part—(1) Green Center field: usually moderate yellow green (5 GY 7/4) (7.5 GY 6/4) (5 GY 6/4) (7.5 GY 7/4) in mature growth. (2) Albino border area: usually light yellowish pink (near 10 R 8/4) (near 7.5 R 8/4) (near 5 Y 8/4) (near 2.5 YR 8/4) (near 5 YR 8/4) (10 R 9/4), moderate yellowish pink (near 7.5 R 8/4) (near 10 R 8/4) (near 2.5 YR 7/4) (near 2.5 YR 8/4) (near 5 YR 8/4), grayish yellowish pink (near 2.5 YR 8/2), pale yellowish pink (near 2.5 YR 8/2) (near 7.5 YR 8/2), brownish pink (near 7.5 YR 8/2), pale orange yellow (near 7.5 YR 8/4) (near 10 YR 9/2), pale yellow (near 5 Y 9/2) (2.5 Y 9/4) (near 2.5 Y 9/2) (near 7.5 Y 9/2) (5 Y 9/4), yellowish white (near 2.5 Y 9/2) (near 5 Y 9/2) (near 7.5 Y 9/2) (10 Y 9/1) and/or pale yellow green (10 Y 9/2) in mature blades.

Inflorescene: has structural characteristics normally identifiable with *Hoya carnosa compacta* variety.

(*A*) *Form.*—Simple umbel with minute 5-merous bracts and usually 20 to 45 flowers in a cluster.

(*B*) *Peduncles.*—(1) General: hard, flesh. (2) Texture: slightly pubescent and with age becoming glaucous and ultimately covered with thick waxy scale. (3) Size: (a) Length—usually between 5 and 15 mm. at maturity. (b) Diameter—usually between 1 and 4 mm. at maturity. (c) Color—usually dark grayish reddish brown (7.5 R 2/2), grayish reddish brown (10 R 3/2) (2.5 YR 3/2), grayish brown (5 YR 3/2), brownish gray (10 YR 3/1) and/or dark grayish yellowish brown (10 YR 3/2) prior to becoming glaucous.

(*C*) *Pedicels.*—(1) General: soft, flesh. (2) Texture: sparsely pubescent. (3) Size: (a) Length—usually between 15 and 28 m. at maturity. (b) Diameter—usually between .7 and 1.7 m. at maturity. (4) Color: commonly light reddish brown (2.5 YR 5/4), and/or light brown (5 YR 5/4) (5 YR 6/4) at maturity.

(*D*) *Flowers.*—(1) General: complete, perfect actinomorphic and 5-merous type flower with hypogynous perianth and alternate sepal-petal and petal-corona segment arrangements. (2) Size: usually between 12 and 18 mm. in overall diameter. (3) Calyx: (a) General—5-merous with separate, valvate sepals. (b) Sepal texture—(1) Upper epidermis: smooth, glabrous. (2) Lower epidermis: sparsely pubescent. (c) Sepal size—proximal to distal end length is usually about 2.5 to 3.0 mm. (d) Sepal color—usually grayish purplish red (10 RP 4/4) (7.5 RP 5/6) (10 RP 5/6) (10 RP 4/6) and/or moderate purplish red (7.5 RP 4/8) (10 RP 5/8). (4) Corolla: (a) General—5-merous, valvate and rotate with interpetal basal fusion for about ½ petal length. (b) Petal texture—(1) Upper epidermis: very dense velvety pubescence. (2) Lower epidermis: glaucous and waxy. (c) Petal size—proximal to distal end length usually about 6 to 7 mm. (d) Petal color—(1) Upper epidermal side: commonly pale purplish pink (7.5 RP 8/4), light pink (near 5 R 8/4) (near 10 RP 8/4) (near 10 RP 8/6) (near 2.5 R 8/4) (near 2.5 R 8/6), moderate pink 10 RP 7/4) (near 10 RP 8/6) (2.5 R 7/4) (10 RP 7/6) (5 R 7/4) (near 10 RP 8/4) (near 5 R 8/4) (2.5 R 8/6) (near 2.5 R 8/4), moderate yellowish pink (7.5 R 7/4) (7.5 R 7/6) (near 10 R 8/4), light yellowish pink (near 10 R 8/4) and/or pale yellowish pink (10 R 9/2). (2) Lower epidermal side: commonly light pink (near 2.5 R 8/4) (near 10 RP 8/4) (7.5 RP 8/4) (near 5 R 8/4), moderate pink (near 2.5 R 8/4) (10 RP 7/4) (near 10 RP 8/4) (near 7.5 RP 8/4), pale pink (5 R 9/2) and/or pale yellowish pink (10 R 9/2). (5) Corona: (a) General—5-merous, horn-like segments which are adnate to stigma and corolla and crested at their proximal ends. (b) Segment texture—hard, smooth, wary and glabrous. (c) Segment color—(1) Proximal end: commonly dark red (2.5 R 3/6) and/or grayish purplish red (10 RP 4/6) (7.5 RP 4/6) (10 RP 5/6) and merging with distal end color. (2) Disal end: commonly yellowish white (5 Y 9/1) (10 Y 9/1) (near 7.5 9/2) (near 5 Y 9/2), pale yellow (near 7.5 Y 9/2) (near 5 Y 9/2) and/or pale yellow green (10 Y 9/2) and merging with proximal end color. (6) Androecium: (a) General—5-merous pollinium pairs partially enclosed by expanded translucent parenchymatous translators and attached to stigma through corpuscula located between adjacent segments and with pollinia and translators rising above corpuscula and stigma in converging conical arrangement. (b) Pollinium color—usually vivid yellow (5 Y 8/12), strong yellow (near 5 W 8/10) (near 2.5 Y 8/8) and/or brilliant yellow (near 5 Y 8/10) (near 2.5 Y 8/8). (7) Gynoecium: (a) General—compound and apocarpous pistil with common stigma. (b) Stigma—(1) General: 5-lobed and waxy. (2) Color: commonly light yellow (near 5 Y 8/6) (near 2.5 Y 8/8), moderate yellow (near 5 Y 8/6) (near 2.5 Y 8/8), brilliant yellow (near 2.5 Y 8/8) and/or strong yellow (near 2.5 Y 8/8). (c) Style—lacking. (d) Ovary—(1) General: two monocarpellate ovularies with axiliary placentation of ovules. (2) Color: commonly grayish purplish red (10 RP 5/6).

The above description is based on observations of well fertilized plants of less than two years old from initial propagation and which were grown under 85% shaded nursery conditions in the Winter Garden, Fla. area and wherein temperatures range approximately from 60–85° F. during the winter months and from 75–95° F. during the summer months.

The following is a general description of a plant of the new variety which was propagated from a stem cutting, the description being taken in the month of January, about two years after the cutting was first planted in a nursery at Winter Garden, Florida.

Stem:

(*A*) *Length.*—About 127 mm. from break to tip.

(*B*) *Number of nodes.*—55 mature nodes plus 5 with embryonic leaves.

(*C*) *Diameter.*—Ranges from about 1 mm. at tip to about 5 mm. near the rooted cutting.

(*D*) *Internode distance.*—Varies from about 10 mm. to about 25 mm.

(*E*) *Color.*—Moderate olive brown (near 2.5 Y 4/2), light olive (10 Y 5/4) (10 Y 5/6) and moderate olive (7.5 Y 4/4).

Leaves:

(*A*) *Number of nonembryonic leaves.*—110 mature plus 8 immature including 6 newly immature (less than 15 days old).

(*B*) *Petioles.*—(1) Diameter—vary from 2 to 3 mm. at maturity. (2) Length—vary from 6 to 10 mm. at maturity. (3) Color—dark red (2.5 R 3/4), grayish red (2.5 R 4/6) and grayish yellowish brown (near 10 YR 4/4) in young growth less than 6 months old and grayish red (2.5 R 5/6), light olive (5 Y 4/4) and moderate olive green 2.5 GY 6/4) (2.5 GY 5/4) in older growth.

(*C*) *Blades.*—(1) Maximum width—vary from 24 to 38 mm. at maturity. (2) Maximum length—vary from 42 to 70 mm. at maturity. (3) Color—(a) Upper epidermal albino border area—strong pink (2.5 R 7/8), strong yellowish pink (near 10 R 7/8), light yellowish pink (near 2.5 YR 8/4) and moderate yellowish pink (near 2.5 YR 8/4) in young mature leaves less than than 6 months old and pale yellow green, (10 Y 9/2), light greenish yellow (7.5 Y 9/6) pale greenish yellow (10 Y 9/4) (7.5 Y 9/4), yellowish white (near 7.5 Y 9/2) and pale yellow (near 7.5 Y 9/2) in growth generally older than 1 year. (b) Upper epidermal green center field—moderate olive green (2.5 GY 4/4) (7.5 GY 4/6) (5 GY 4/4) and moderate yellow green (5 GY 5/6) in mature leaf blades. (c) Lower epidermal border area—light yellowish pink (near 5 YR 8/4), moderate yellowish pink (near 5 YR 8/4), pale orange yellow (near 7.5 YR 8/4), pale yellow (2.5 Y 9/4), yellowish white (7.5 Y 9/2) and pale yellow green (10 Y 9/2) in mature growth. (d) Lower epidermal green center field—moderate yellow green (5 GY 7/4) (5 GY 6/4).

The following is a general description of a typical inflorescence which appeared on a vine about 2 years old Number of flower: 27.

Peduncle:

(*A*) *Size.*—(1) Length: 9 mm. (2) Diameter: about 3 mm.

(*B*) *Color.*—Grayish reddish brown (2.5 YR 3/2) and grayish brown (5 YR 3/2).

Pedicels:

(*A*) *Size.*—(1) Length: vary from about 20 to 24 mm. (2) Diameter: about 1 mm. average.

(*B*) *Color.*—Light reddish brown (2.5 YR 5/4) and light brown (5 YR 5/4).

Flowers:

(*A*) *Size.*—14 to 17 mm. in diameter.

(*B*) *Sepal size.*—Proximal to distal end length about 2.5 mm.

(*C*) *Sepal color.*—Grayish purplish red (7.5 RP 5/6) (10 RP 5/6).

(*D*) *Petal size.*—Proximal to distal end length about 6 mm.

(*E*) *Petal color.*—(1) Upper epidermal side: moderate pink (5 R 7/4) and moderate yellowish pink (7.5 R 7/4). (2) Lower epidermal side: moderate pink (near 2.5 R 8/4).

(*F*) *Corona segment color.*—(1) Proximal end: grayish purplish red (10 RP 4/6) and merging with distal end color. (2) Distal end: plate yellow green (10 Y 9/2) and merging with proximal end color.

(*G*) *Pollinium color.*—Strong yellow (near 5 Y 8/10).

(*H*) *Stigma color.*—Moderate yellow (near 5 Y 8/6).

(I) *Ovary color.*—Grayish purplish red (10 RP 5/6).

I claim:

1. The new and distinct variety of the milkweed family substantially as herein described and characterized in particular by a growth habit providing specimens which are structurally closely similar in appearance to plant specimens of the *Hoya carnosa compacta* variety, which have leaf blades characterized by an albino border area that surrounds a solid green center field in the upper epidermal part of the blade and which are further characterized by an albino border area that surrounds a solid green center field in the lower epidermal part of the blade.

No references cited.

ROBERT E. BAGWILL, Primary Examiner

PO-1050
(5/69)

UNITED STATES PATENT OFFICE
CERTIFICATE OF CORRECTION

Patent No. Plant Patent No. 3310 Dated February 27, 1973

Inventor(s) Barnell L. Cobia

It is certified that error appears in the above-identified patent and that said Letters Patent are hereby corrected as shown below:

Column 2, Line 46, delete "(Ascleipiadecease)" and substitute -- (Asclepiadaceae) --;
Column 4, Line 26, delete "Inflorescene" and substitute -- Inflorescence --;
Line 43, delete "1.7 m." and substitute -- 1.7 mm. --;
Column 5, Line 10, delete "wary" and substitute -- waxy --;
Line 14, delete "Disal" and substitute -- Distal --;
Line 26, delete "(near 5 W 8/10)" and substitute -- (near 5 Y 8/10) --;
Column 6, Line 7, delete "than" (second occurrence);

Signed and sealed this 31st day of July 1973.

(SEAL)
Attest:

EDWARD M.FLETCHER,JR.
Attesting Officer

RENE D. TEGTMEYER
Acting Commissioner of Patents